United States Patent [19]

Fujiwara et al.

[11] Patent Number: 4,536,324
[45] Date of Patent: Aug. 20, 1985

[54] NONIONIC SURFACTANT TYPE VESICLE DISPERSION

[75] Inventors: Masami Fujiwara, Kawasaki; Hidenori Fukuda, Minami-ashigara; Minako Tanaka, Yokohama, all of Japan

[73] Assignee: Lion Corporation, Tokyo, Japan

[21] Appl. No.: 514,789

[22] Filed: Jul. 18, 1983

[30] Foreign Application Priority Data

Jul. 19, 1982 [JP] Japan ................................ 57-125315

[51] Int. Cl.$^3$ .............................................. B01J 13/00
[52] U.S. Cl. .................................... 252/311; 252/312; 264/4.1
[58] Field of Search ................... 252/311, 312; 264/4.1

[56] References Cited

U.S. PATENT DOCUMENTS

| 4,217,344 | 8/1980 | Vanlerberghe et al. | 264/4.1 |
| 4,344,968 | 8/1982 | Aoda et al. | 424/365 |
| 4,350,705 | 9/1982 | Hamano et al. | 424/278 |

FOREIGN PATENT DOCUMENTS 1539625 1/1979 United Kingdom .

OTHER PUBLICATIONS

Okahata et al., Journal of Colloid & Interface Science, vol. 82, No. 2, 1981, pp. 401–417.
Hisao Tsutsumi, "Solution Behavior of Nonionic Surfactants with Multi Hydrophobic Chains in Water", Nippon Kagaka Kaishi, 1981, (11), pp. 1691–1696.

Primary Examiner—Edward A. Miller
Assistant Examiner—Anne Brookes
Attorney, Agent, or Firm—Armstrong, Nikaido, Marmelstein & Kubovcik

[57] ABSTRACT

A nonionic surfactant type vesicle dispersion comprising vesicles, dispersed in an aqueous medium, composed of (A) 100 parts by weight of at least one ethoxylate selected from the group consisting of polyoxyethylene castor oil ethers and polyoxyethylene hardened castor oil ethers and (B) 3 to 30 parts by weight of sorbitan polyesters of long-chain fatty acids.

This nonionic surfactant type vesicle dispersion can include a hydrophilic or hydrophobic effective component in a state isolated from an aqueous medium.

3 Claims, No Drawings

NONIONIC SURFACTANT TYPE VESICLE DISPERSION

BACKGROUND OF THE INVENTION

1. Field of the Invention

This invention relates to a vesicle dispersion utilizing a readily available nonionic surfactant, which is capable of maintaining a hydrophilic or hydrophobic effective component in an isolated state from an aqueous dispersion medium.

2. Description of the Prior Art

It is known in the art that an amphiphatic substance can form vesicles in water. For example, vesicles such as liposomes based on phosphatides or phospholipids and ufasomes based on unsaturated fatty acids are present in natural substances. Attempts have been made to use these natural vesicles in the fields of cosmetics and pharmaceuticals since these types of vesicles are stable dispersions and are safe to use. However, these natural vesicles are not suitable for use in large volume consumption because of their relatively high cost.

Recently, vesicles or niosomes utilizing readily available nonionic surfactants have been found. For example, it has been reported in Japanese Unexamined Patent Publication (Kokai) No. 52-6375 that vesicle dispersions are formed from nonionic surfactants having the general formula:

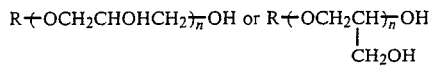

wherein R represents an aliphatic hydrocarbon group having 12 to 30 carbon atoms and n represents an integer of 1 to 6. It has also been reported in J. Colloid Interface Sci., Vol. 82, No. 2, 401–417 (1981) that vesicles are formed from ethylene oxide addition products of glycerin dialkyl ethers or ethylene oxide addition products of myristic acid stearyl amides. On the other hand, it has been reported in Nippon Kagaku Kaishi, 1981 (11), p. 1691–1696 that polyoxyethylene hardened castor oil ethers and polyoxyethylene sorbitol tetraoleate form concentric lamella type liquid crystals.

Vesicles can be considered to be special forms of concentric lamella type liquid crystals. Vesicles are different from the concentric lamella type liquid crystals since water or an aqueous solution can be contained in substantially hydrophillic cavities formed in the inside of bimolecular or multiple layer membranes (or films) formed from a surfactant. Accordingly, it is necessary that the surfactant molecules be oriented so as to form lamella bimolecular membranes having a curvature capable of readily forming vesicles. However, although the above-mentioned polyoxyethylene hardened castor oil ethers form concentric lamella type liquid crystals, the polyoxyethylene hardened castor oil ethers cannot form uniform state concentric lamella type liquid crystals and clear vesicle structures due to the distribution of the ethylene oxide addition mole number, since the polyoxyethylene hardened castor oil ethers are mixtures of the plural compounds having different ethylene oxide addition mole number.

SUMMARY OF THE INVENTION

The object of the present invention is to develop a vesicle dispersion from a readily available surfactant, which is acceptable by official authorities for use in foods and cosmetics.

Other objects and advantages of the present invention will be apparent from the following description.

In accordance with the present invention, there is provided a nonionic surfactant type vesicle dispersion comprising vesicles, dispersed in an aqueous medium, composed of (A) 100 parts by weight of at least one ethoxylate selected from the group consisting of polyoxyethylene castor oil ethers and polyoxyethylene hardened castor oil ethers and (B) 3 to 30 parts by weight of sorbitan polyesters of long-chain fatty acids.

DESCRIPTION OF THE PREFERRED EMBODIMENTS

The inventors have found that nonionic surfactants of polyoxyethylene castor oil ethers and polyoxyethylene hardened castor oil ethers can be oriented, by adding sorbitan polyesters of long-chain fatty acids, with such a curvature that vesicles are readily formed.

The nonionic surfactants which form films of vesicles usable as component (A) of the vesicle dispersion according to this invention are polyoxyethylene castor oil ethers or polyoxyethylene hardened castor oil ethers. These ethoxylates have the following general formula:

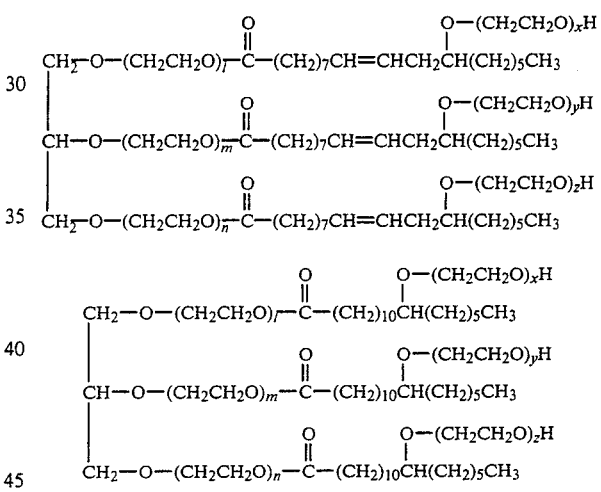

These ethoxylates can be used alone or in any mixture thereof. The average ethylene oxide addition mole number (i.e., $l+m+n+x+y+z$ in the above formula) of these ethoxylates is generally 7 to 20, desirably 8 to 15.

The sorbitan polyesters of long-chain fatty acids usable as component (B) of the vesicle dispersion according to this invention are those having long-chain fatty acid residues with 14 to 18 carbon atoms, desirably 16 to 18 carbon atoms. Furthermore, the esterification degree of the sorbitan polyesters of long-chain fatty acids is desirably 2.5 to 3.5, especially 2.8 to 3.2. Typical examples of these sorbitan polyesters of long-chain fatty acids are sorbitan tripalmitate, sorbitan trioleate, and sorbitan tallow fatty acid triesters.

According to this invention, component (B) should be used in an amount of 3 to 30 parts by weight, desirably 5 to 25 parts by weight, based on 100 parts by weight of the component (A). When component (A) is used alone, concentric lamella type liquid crystals are formed but the formation of vesicles cannot be observed by an electron microscope. However, the addition of a small amount of component (B) to component (A) results in the orientation of the surfactants with such a curvature that vesicles are readily formed. Thus, the desired vesicles are formed. When the weight ratio of components (A) and (B) are within the above-mentioned range of this invention, substantially all associates or aggregates formed by the surfactants form vesicles. The above-mentioned desired range is selected based on the stability of the formed vesicles and the maintenance (or keeping properties) of various agents (or effective components) supported with the vesicles. An amount of component (A) of more than 30 parts by weight based on 100 parts by weight results in the destruction of the vesicles (or the formation of the emulsions).

The vesicle dispersions of this invention can be prepared by, for example, mixing components (A) and (B) to form a homogeneous phase, followed by mixing with a large amount of water. In this case, the total amount of components (A) and (B) is desirably 0.1% to 50% by weight, more desirably 1% to 35% by weight, based on the total weight of the dispersion. The resultant vesicle dispersion can be diluted with water or an aqueous solution to any concentration. The mixing methods of components (A) and (B) and the mixing methods thereof with water in the preparation of the vesicle dispersion are not specifically limited and may be any conventional mixing methods. For example, conventional mechanical agitation methods and ultrasonic treatments can be used. When a mixing method with a relatively low shearing force such as mechanical mixing is used, vesicles having a particle diameter of about 1 to 5 $\mu$m are obtained. On the other hand, vesicles having a particle diameter of about 0.1 to 1 $\mu$m are obtained in the case of the ultrasonic treatment.

The vesicle dispersion of this invention can contain a small amount of ionic surfactants for changing the surface charge of the vesicles and, optionally, hydrophilic and hydrophobic (or lipophilic) agents (i.e., effective components) in the inside of the vesicle or the membrane.

The ionic surfactants optionally usable, as a component for changing a surface charge of the vesicles, in the vesicle dispersion of this invention are cationic surfactants and anionic surfactants. Examples of the cationic surfactants are long-chain alkylamines having 14 to 22 carbon atoms such as palmitylamine, stearylamine, and hardened tallow alkylamines, and the salts thereof; di (long-chain alkyl) amines having 14 to 22 carbon atoms such as dipalmitylamine, distearylamine, and di (hardened tallow alkyl) amines, and the salts thereof; monoalkyl type quaternary ammonium salts having an alkyl group with 14 to 22 carbon atoms such as palmityl trimethyl ammonium salts, stearyl trimethyl ammonium salts, oleyl trimethyl ammonium salts, and hardened tallow alkyl trimethyl ammonium salts; dialkyl type quaternary ammonium salts having two alkyl groups with 14 to 22 carbon atoms such as distearyl dimethyl ammonium salt, and di (hardened tallow alkyl) dimethyl ammonium salts; alkylene oxide addition products of long-chain alkylamines having an alkyl group with 14 to 22 carbon atoms such as bishydroxyethyl steary amine, bishydroxyethyl hardened tallow alkyl amine, and polyoxyethylene stearyl amine, and the salts thereof; and 2-alkyl substituted imidazolinium salts having an alkyl group with 14 to 22 carbon atoms such as quaternary products of dehydrated cyclized products of stearic acid and hydroxyethyl ethylenediamine.

Examples of anionic surfactants are: phosphoric mono- and di-esters of long-chain alcohols having 14 to 22 carbon atoms and the salts thereof; phosphoric mono-and di-esters of alkylene oxide addition products of long-chain alcohols having 14 to 22 carbon atoms and the salts thereof; alkylsulfates having 14 to 22 carbon atoms; polyoxyethylene alkyl ether sulfates of alcohols having 14 to 22 carbon atoms; alkane sulfonates having 14 to 22 carbon atoms; and olefin sulfonates having 14 to 22 carbon atoms.

The lipophilic substances optionally contained in the inside of the vesicles of the dispersions of this invention are, for example, lipophilic agents usable as an effective or active component in pharmaceuticals. Examples of these agents include $\beta$-glycyrrhetinic acid, triamcinolone acetomide, hydrocortisone acetate; oily components or fats and oils such as fatty acid esters, squalane, liquid paraffin; or other lipophilic substances having a polar group such as chlorohexidine. These substances can be used in any amount as long as the vesicle formation ability of components (A) and (B) is not impaired.

The hydrophilic substances optionally contained in the inside of the vesicles of the dispersion of this invention are, for example, hydrophilic agents usable as an effective or active component in pharmaceuticals. Examples of these substances include dipotassium $\beta$-glycyrrhetinate, chlorohexidine digluconate; humectants having humidity maintaining effects to human skins such as amino acids, pyrrolidone carboxylate, hyaluronic acid, glycerin; or water-soluble substances capable of reacting with a component contained in the water phase outside the vesicles. These hydrophilic substances can be used in any amount, as in the lipophilic substances, as long as the vesicle formation ability of components (A) and (B) is not impaired.

The incorporation of the above-mentioned lipophilic or hydrophilic substances can be effected by, for example, mixing components (A) and (B) and the above-mentioned lipophilic or hydrophilic substances together to form a homogeneous phase, followed by the mixing with a large amount of water.

The vesicle dispersion of this invention can contain various kinds of effective components in the water phase in the inside of the vesicles or in the membrane of the vesicles and, therefore, the vesicle dispersion can be used as a carrier for supporting the effective components. Furthermore, the membrane component forming the vesicles is a surfactant having strong lipophilic nature and, therefore, the vesicles themselves have an action as an oily component of cosmetics. Consequently, the vesicle dispersion of this invention can be desirably used in pharmaceuticals and emulsion type cosmetics such as creams and milky lotions. When the vesicle dispersion of the present invention is used in the above-mentioned application fields, the necessary components can be added to the vesicle dispersion during the preparation step thereof. The resultant vesicle dispersion can be directly used. Alternatively, the vesicle dispersion thus obtained can be added to an aqueous solution or dispersion containing the necessary components or can be simply diluted with water.

The vesicle dispersion according to this invention has an extremely high practical utility. Substantially all associates or aggregates are formed from the surfactants used, the resultant dispersion is stable for a long term, it is available at a low cost, and is safe. Further a readily available surfactant is used for the formation of the vesicle dispersion.

Furthermore, the following advantages can be obtained by the vesicle dispersion according to the present invention:

(1) A component which should not be mixed with an aqueous phase in the outside of the vesicles can be retained in the inside (i.e., an aqueous phase) of the vesicles or in the membrane, or in both the inside of the vesicles and the membrane.

(2) The membrane forming the vesicles has a structure similar to that of a cell membrane. Therefore, the vesicle dispersion of this invention has a strong affinity or interaction to vital membranes, has excellent adsorptivity to vital tissues, can be retained on a vital surface for a relatively long term, and affords good absorbability of the effective components contained in the inside of the vesicles or the membrane into the inside of a vital body.

(3) The vesicles of this invention have a stability superior to those of an emulsion including a microemulsion and a multi-phase emulsion and are stably present even in a diluted solution.

Furthermore, the formation of vesicles can be basically confirmed by observation (e.g., visual observation and micrographs) of an electron microscope. However, the formation of vesicles can be approximately estimated by the presence or absence of a cross-nicols in a polarized microscope.

EXAMPLE

The present invention now will be further illustrated by, but is by no means limited to, the following examples, in which all percents are by weight unless otherwise specified.

EXAMPLE 1

A 9 g amount of polyoxyethylene hardened castor oil ether having an average ethylene oxide addition mole number ($\bar{p}$) of 10 (i.e., component $A_1$) and 1 g of sorbitan trioleate (i.e., component B) were weighed and were thoroughly mixed together at a room temperature in a 100 ml volume beaker. Then, 90 g of water was added to the resultant mixture and was thoroughly mixed at a room temperature to form a uniform opaque white milky vesicle dispersion having flowability or fluidity.

The formation of the vesicles was visually confirmed by an electron microscope. The particle diameters of the vesicles were within the range of 1 to 5 $\mu$m.

EXAMPLE 2

A vesicle dispersion was prepared in the same manner as Example 1, except that polyoxyethylene castor oil ether ($\bar{p}=10$) was used in lieu of component $A_1$ of Example 1.

The formation of vesicles in the resultant dispersion was visually confirmed by an electron microscope. The particle diameters of the vesicles were 1 to 5 $\mu$m.

EXAMPLE 3

A 9 g amount of component $A_1$ of Example 1 and 1 g of component B of Example 1 were thoroughly mixed in a 100 ml volume beaker. A 0.1 g amount of $\beta$-glycyrrhetinic acid was added to the resultant mixture to dissolve the same in the mixed surfactant phase and, then, 89.9 g of water was added to the mixture to obtain the homogeneous mixture. The mixing procedures were carried out at a room temperature.

Thus, a milky dispersion having fluidity was obtained. The particle diameters of the vesicles in the dispersion were 1 to 5 $\mu$m.

EXAMPLE 4

A 9 g amount of component $A_1$ of Example 1 and 1 g of component B of Example 1 were thoroughly mixed in a 100 ml volume beaker. A 10 g amount of a 5% aqueous solution of sodium pyrrolidone carbonate was added to the resultant mixture to form a homogeneous mixture. Then, 80 g of a 0.43 M aqueous dextrose solution was added to and mixed homogeneously with the mixture. The mixing operations were carried out at a room temperature.

Thus, a milky dispersion having fluidity was obtained. The particle diameters of the vesicles in the dispersion were 1 to 5 $\mu$m.

EXAMPLE 5

A 9 g amount of component $A_1$ of Example 1 and 1 g of component B were thoroughly mixed in a 100 ml volume beaker. A 90 g amount of a 5% aqueous solution of sodium pyrrolidone carbonate was added to the resultant mixture. The mixture was thoroughly mixed to form a homogeneous mixture. The above mixing procedures were carried out at a room temperature.

Thus, a milky dispersion having fluidity was obtained. The particle diameters of the vesicles in the dispersion were 1 to 5 $\mu$m.

EXAMPLE 6

A 9 g amount of component $A_1$ of Example 1 and 1 g of component B of Example 1 were thoroughly mixed in a 100 ml volume beaker. To the resultant mixture, 0.1 g of $\beta$-glycyrrhetinic acid was added to dissolve the same in the mixed surfactant phase and, then, 10 g of a 0.1% aqueous solution of chlorohexidine-2-gluconate was added and mixed to form a homogeneous mixture. Thereafter, 80 g of a 0.002 M aqueous sodium chloride solution was added to and mixed with the mixture above to form a homogeneous mixture. The above procedures were carried out at a room temperature.

Thus, a milky mixture having fluidity was obtained. The particle diameters of the vesicles were 1 to 5 $\mu$m.

EXAMPLE 7

A 9 g amount of component $A_1$ and 1 g of component B were thoroughly mixed in a 100 ml volume beaker and, then, 90 g of water was added to obtain a homogeneous mixture. The resultant vesicle dispersion was entirely subjected to ultrasonic irradiation.

The finally obtained mixture was translucent and contained vesicles having a particle diameter of 0.1 to 1 $\mu$m.

We claim:

1. A nonionic surfactant type vesicle dispersion comprising vesicles, dispersed in an aqueous medium, composed of (A) 100 parts by weight of at least one ethoxylate selected from the group consisting of polyoxyethylene castor oil ethers and polyoxethylene hardened castor oil ethers having an average ethylene oxide addition mole number of 7 to 20 and (B) 3 to 30 parts by weight of sorbitan polyesters of long-chain fatty acids having 14 to 18 carbon atoms, and having the esterification degree of 2.5 to 3.5, wherein the total amount of components (A) and (B) is about 0.1% to 50% by weight based on the total weight of the dispersion.

2. A vesicle dispersion as claimed in claim 1, wherein said sorbitan polyesters are sorbitan polyesters of long-chain fatty acids having 16 to 18 carbon atoms.

3. A vesicle dispersion as claimed in claim 1, wherein the weight ratio of component (A) to component (B) is 100:5 to 100:25.

* * * * *